(12) United States Patent
Sekiguchi et al.

(10) Patent No.: US 11,685,915 B2
(45) Date of Patent: Jun. 27, 2023

(54) METHOD OF COLLECTING NUCLEIC ACID

(71) Applicant: Toray Industries, Inc., Tokyo (JP)

(72) Inventors: Shota Sekiguchi, Kamakura (JP); Taiga Arai, Kamakura (JP); Masateru Itou, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 244 days.

(21) Appl. No.: 16/957,400

(22) PCT Filed: Dec. 26, 2018

(86) PCT No.: PCT/JP2018/047845
§ 371 (c)(1),
(2) Date: Jun. 24, 2020

(87) PCT Pub. No.: WO2019/131760
PCT Pub. Date: Jul. 4, 2019

(65) Prior Publication Data
US 2020/0332277 A1    Oct. 22, 2020

(30) Foreign Application Priority Data
Dec. 27, 2017  (JP) .............................. JP2017-250916

(51) Int. Cl.
*G01N 33/00* (2006.01)
*C12N 15/10* (2006.01)
*C07H 21/04* (2006.01)

(52) U.S. Cl.
CPC ..................................... *C12N 15/10* (2013.01)

(58) Field of Classification Search
None
See application file for complete search history.

(56) References Cited

U.S. PATENT DOCUMENTS

| | | | |
|---|---|---|---|
| 6,383,393 B1 | 5/2002 | Colpan et al. | |
| 9,493,828 B2 * | 11/2016 | Rava et al. | C12Q 1/6827 |
| 2002/0177139 A1 | 11/2002 | Greenfield et al. | |
| 2003/0228602 A1 * | 12/2003 | Parker | C12P 19/34 |
| | | | 435/6.12 |
| 2005/0037351 A1 | 2/2005 | Kanno et al. | |
| 2005/0059024 A1 * | 3/2005 | Conrad | C12N 15/1003 |
| | | | 536/25.4 |
| 2005/0208510 A1 | 9/2005 | Latham et al. | |
| 2006/0166241 A1 | 7/2006 | Shim et al. | |
| 2006/0177855 A1 | 8/2006 | Utermohlen et al. | |
| 2008/0138884 A1 | 6/2008 | Takeshita et al. | |
| 2008/0145910 A1 * | 6/2008 | Ward et al. | C12Q 1/6848 |
| | | | 435/193 |
| 2008/0187979 A1 | 8/2008 | Mori | |
| 2008/0261857 A1 * | 10/2008 | Orlich et al. | C11D 11/04 |
| | | | 510/445 |
| 2011/0172405 A1 * | 7/2011 | Dhulipala et al. | C12N 15/111 |
| | | | 536/23.1 |
| 2011/0319506 A1 | 12/2011 | Erbacher et al. | |
| 2015/0218550 A1 * | 8/2015 | Stead et al. | C12N 15/1003 |
| | | | 210/287 |
| 2017/0016047 A1 | 1/2017 | Southern et al. | |
| 2017/0029808 A1 | 2/2017 | Tsukamoto | |
| 2018/0051274 A1 | 2/2018 | Sekiguchi et al. | |
| 2019/0085317 A1 * | 3/2019 | Sekiguchi et al. | C12N 15/1006 |
| 2019/0203200 A1 | 7/2019 | Nakagawa et al. | |

FOREIGN PATENT DOCUMENTS

| | | |
|---|---|---|
| CN | 1539013 A | 10/2004 |
| CN | 1922318 A | 2/2007 |
| CN | 10111597 A | 1/2008 |
| CN | 101120089 A | 2/2008 |
| CN | 107663521 A | 2/2018 |
| JP | 8-501321 A | 2/1996 |
| JP | 2003-235555 A | 8/2003 |
| JP | 2007-006728 A | 1/2007 |
| JP | 2007-529229 A | 10/2007 |
| JP | 2008-527973 A | 7/2008 |
| JP | 2012-513386 A | 6/2012 |
| WO | 2005/068628 A2 | 7/2005 |
| WO | 2015/120447 A1 | 8/2015 |
| WO | 2015/132615 A1 | 9/2015 |
| WO | 2015/159979 A1 | 10/2015 |
| WO | 2016/152763 A1 | 9/2016 |
| WO | WO-2017159763 A1 * | 9/2017 ............. C12N 15/09 |
| WO | 2018/052011 A1 | 3/2018 |

OTHER PUBLICATIONS

The Extended European Search Report dated Sep. 21, 2021, of counterpart European Application No. 18896548.7.
First Office Action dated Feb. 18, 2023, of counterpart Chinese Patent Application No. 201880083687.6, along with an English translation.
S. Tang et al., "Principles and Method Science of Nucleic Acid Separation and Purification," Sect. Clin. Biochem. & Lab Med. Foreign Med. Sci., vol. 26, No. 3, pp. 192 and 193, Mar. 2005, along with an English translation.

* cited by examiner

Primary Examiner — Bradley L. Sisson
(74) Attorney, Agent, or Firm — DLA Piper LLP (US)

(57) ABSTRACT

A method utilizes an aluminum oxide support with a water-soluble neutral polymer adsorbed on a surface of the aluminum oxide support and is aimed to collect nucleic acids from a body fluid sample. The method includes a step of adsorbing nucleic acids on the support in the presence of a chaotropic agent and a step of adding a solution containing an anionic surfactant to the nucleic acid-adsorbed support.

10 Claims, 2 Drawing Sheets

Specification includes a Sequence Listing.

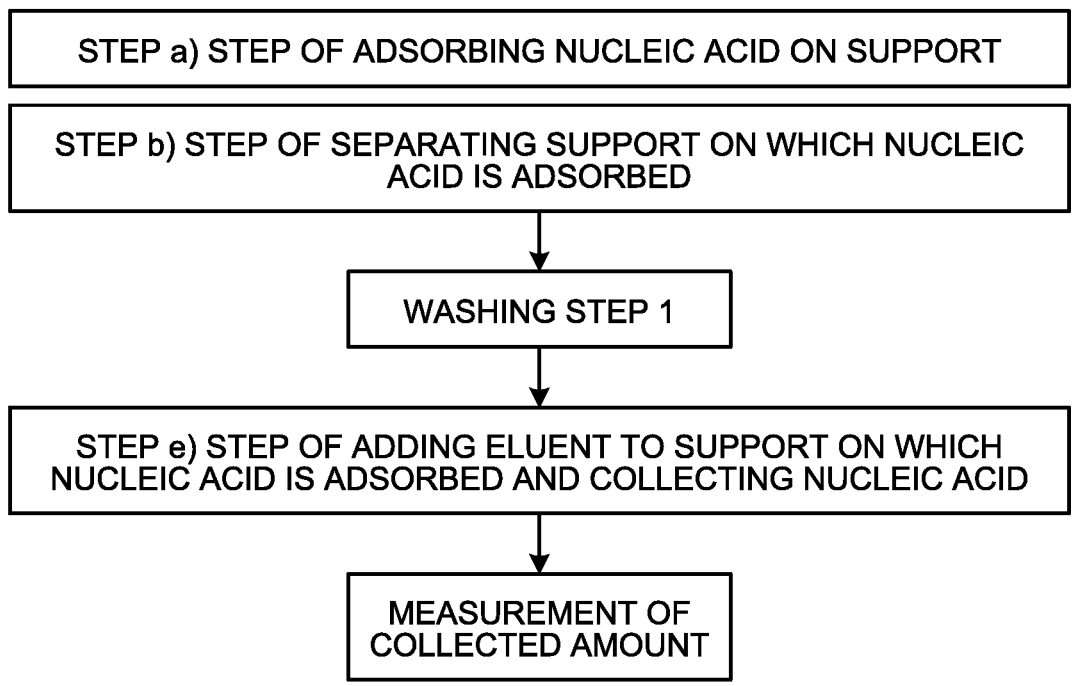

METHOD OF COLLECTING NUCLEIC ACID

TECHNICAL FIELD

This disclosure relates to a method of collecting a nucleic acid(s) from a body fluid sample with a high yield, by using an aluminum oxide support with a water-soluble neutral polymer being adsorbed on a surface thereof, and a kit that collects the nucleic acid(s).

BACKGROUND

The development of experimental techniques using nucleic acids has allowed for a search for a new gene and an analysis of the gene. Screening tests and clinical tests by using gene analysis have been performed in the medical field as well, for example, a human genome has been analyzed to identify a disease such as a cancer, and a pathogen genome has been analyzed to identify a pathogen infection. Particularly, in recent years, detection of genes collected from body fluids such as blood and urine has been expected as a low invasive examination.

Not only long-chain nucleic acids such as genome, but also short chain nucleic acids having not more than 1000 bases has attracted attention as targets for the analysis of gene in such a body fluid. miRNA discovered in recent years is generally a single-stranded RNA with 18 to 25 bases, and is biosynthesized from a pre-miRNA with 60 to 90 bases. They are considered to be related to diseases because they have a function of regulating protein synthesis and gene expression, and have attracted attention as targets for gene analysis. The cell-free DNA (cfDNA) having attracted attention in recent years is a double-stranded DNA having a length of about one to four times of 166 bases corresponding to one unit of histone, and is generated in a process of destroying and decomposing cells. In particular, cell-free DNA derived from cancer cells is referred to as blood circulating tumor DNA (ctDNA) and has a gene mutation specific to the cancers and, therefore, has attracted attention as a target for determination of presence or absence of influence on therapeutic agents as well as inspection of the presence or absence of cancer.

International Publication WO 2016/152763 discloses a method of collecting nucleic acids using an aluminum oxide support on which a water-soluble neutral polymer is adsorbed. According to that method, it is shown that the nucleic acids can be collected with a high yield. Specifically, as illustrated in FIG. 2 described below, the nucleic acids are adsorbed on the support in the presence of a chaotropic agent, and eluted to be collected by adding an eluent to the support on which the nucleic acids are adsorbed.

Although the method described in WO '763 can collect a nucleic acid(s) with a high yield, it has been desired to further improve collection amounts for collecting very small amounts of nucleic acids present in body fluid. For example, the gene mutation specific to cancer described above is present in a very small amount in the body fluid. In addition, the very small amount of nucleic acid is expected to be still present in the body fluid without being collected in conventional methods. To analyze such a nucleic acid, a method of collecting the nucleic acid(s) with a higher yield is required.

SUMMARY

We studied a method capable of collecting a nucleic acid(s) with a higher yield with reference to the method of collecting the nucleic acid(s) disclosed in WO '763. We found that the collection amount of the nucleic acid is further improved by adding a step of mixing a nucleic acid-adsorbed support with a solution containing an anionic surfactant as a preceding step before adding an eluent to the nucleic acid-adsorbed support.

We thus provide:

(1) A method of collecting a nucleic acid(s) from a body fluid sample, the method including the following steps:
   step a) mixing a chaotropic agent and an aluminum oxide support with a water-soluble neutral polymer adsorbed on a surface of the aluminum oxide support, with a solution containing a nucleic acid(s), and adsorbing the nucleic acid(s) to the support;
   step b) separating the support on which the nucleic acid(s) is/are adsorbed from the solution mixed at step a);
   step c) mixing the support separated at step b) with a solution containing an anionic surfactant;
   step d) separating the support on which the nucleic acid(s) is/are adsorbed from the solution mixed at step c); and
   step e) adding an eluent to the support separated at step d) and collecting the nucleic acid(s).

(2) The method according to (1), wherein the nucleic acid is micro RNA or cell-free DNA.

(3) The method according to (1) or (2), wherein the body fluid sample is blood, serum, plasma, urine, or saliva.

(4) The method according to any one of (1) to (3), wherein the anionic surfactant is of carboxylic acid type, sulfonic acid type, or sulfate ester type.

(5) The method according to (4), wherein the anionic surfactant of the carboxylic acid type is caprylic acid salt, pelargonic acid salt, capric acid salt, and lauric acid salt, N-decanoylsarcosine salt, or a N-lauroylsarcosine salt.

(6) The method according to (4), wherein the anionic surfactant of the sulfonic acid type is octylbenzene sulfonate salt or dodecylbenzene sulfonate salt.

(7) The method according to (4), wherein the anionic surfactant of the sulfate ester type is octyl sulfate salt, decyl sulfate salt, or dodecyl sulfate salt.

(8) The method according to any one of (1) to (7), wherein the water-soluble neutral polymer is a polymer having a zeta potential of not less than −10 mV and not more than +10 mV in a solution of pH 7.

(9) The method according to (8), wherein the polymer is polyethylene glycol, polyvinyl alcohol, polyvinylpyrrolidone, poly(2-ethyl-2-oxazoline), or hydroxypropyl methylcellulose.

(10) The method according to any one of (1) to (9), wherein the eluent is a buffer solution.

(11) A kit that collects a nucleic acid(s), the kit comprising an aluminum oxide support with a water-soluble neutral polymer adsorbed on a surface of the aluminum oxide support, a solution containing a chaotropic agent, and a solution containing an anionic surfactant.

We thus enable collection of the nucleic acid(s) with a higher yield than that in conventional methods, and therefore is expected to be capable of collecting very small amount of nucleic acid(s) in body fluid as well as new nucleic acid(s).

BRIEF DESCRIPTION OF THE DRAWINGS

FIG. 2 is an example of a method of collecting a nucleic acid described in WO '763.

DETAILED DESCRIPTION

Figure 1:
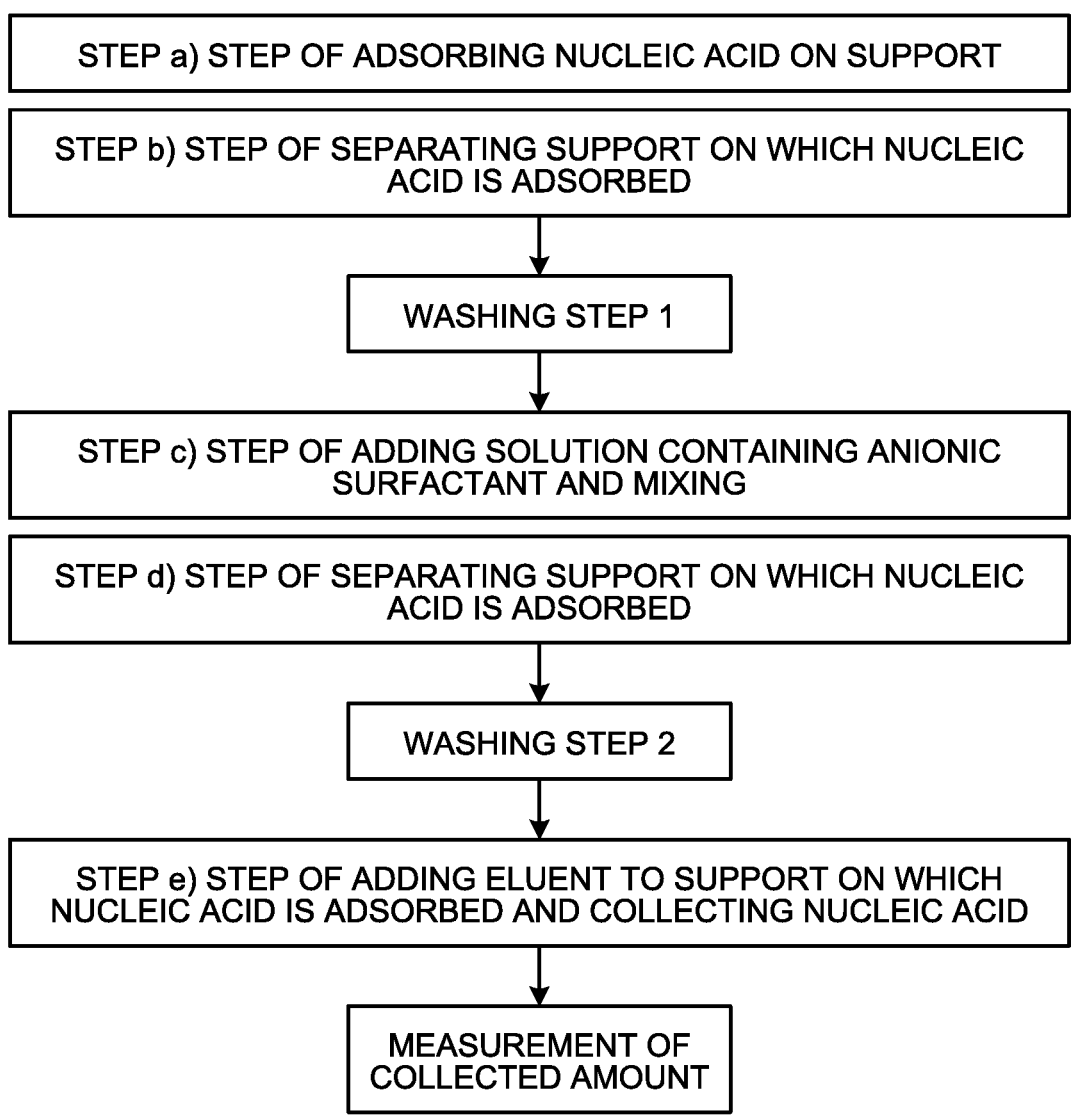
FIG. 1 is a summary representing steps of a method of collecting a nucleic acid.

This disclosure relates to a method of collecting a nucleic acid(s) from a body fluid sample, including the following steps:

step a) mixing a chaotropic agent and an aluminum oxide support with a water-soluble neutral polymer adsorbed on a surface thereof, with a solution containing the nucleic acid(s), and adsorbing the nucleic acid(s) to the support;

step b) separating the support on which the nucleic acid(s) is/are adsorbed from the solution mixed at step a);

step c) mixing the support separated at step b) with a solution containing an anionic surfactant;

step d) separating the support on which the nucleic acid(s) is/are adsorbed from the solution mixed at step c); and step e) adding an eluent to the support separated at step d) and collecting the nucleic acid(s).

In this description, the aluminum oxide support with the water-soluble neutral polymer adsorbed on the surface thereof may be referred to as the support.

As illustrated in FIG. 2, the method of collecting the nucleic acid(s) described in WO '763 is a method including the following steps a), b), and e) as a basic procedure: step a) mixing the chaotropic agent and the aluminum oxide support with the water-soluble neutral polymer adsorbed on the surface thereof, with the solution containing the nucleic acid(s), and adsorbing the nucleic acid(s) to the support; step b) separating the support on which the nucleic acid(s) is/are adsorbed from the solution mixed at step a); and step e) adding the eluent to the support separated at step b) and collecting the nucleic acid.

As illustrated in FIG. 1, we found that the collection amount of the nucleic acid is further improved by adding step c) mixing the support on which the nucleic acid(s) is/are adsorbed with the anionic surfactant, as a preceding step before step e) adding the eluent to the support on which the nucleic acid(s) is/are adsorbed. The method is described below for each step.

Step a) is the step of mixing the chaotropic agent and the support with the solution containing the nucleic acid(s), and adsorbing the nucleic acid(s) to the support. At step a), the support is mixed with the solution containing the nucleic acid(s) in the presence of the chaotropic agent and the nucleic acid(s) is adsorbed to the support.

The method of mixing the chaotropic agent and the support with the solution containing the nucleic acid(s) is not particularly limited. For example, the method may be carried out by pipetting or mixing by inversion, or by a device such as mixer and vortex. The mixing time is not particularly limited, but may be about 5 minutes. The mixing time may be more than 5 minutes. The order of mixing the chaotropic agent, the support and the solution containing the nucleic acid(s) is not particularly limited. For example, the support may be packed in a column to allow the chaotropic agent and the solution containing the nucleic acid to pass therethrough.

The chaotropic agent is a generic term that stands for substances generating a chaotropic ion(s), and is a chemical substance having a property of destabilizing a molecular structure such as a protein. The chaotropic ion is also referred to as a chaotrope. Specific examples of the chaotropic agent include guanidine salts, sodium isocyanate, sodium iodide, potassium iodide, urea, sodium bromide, potassium bromide, calcium bromide, ammonium bromide, sodium perchlorate, sodium thiocyanate, potassium thiocyanate, ammonium isothiocyanate, sodium chloride, potassium chloride, and ammonium chloride. Among them, guanidine salt or urea is preferable. Examples of the guanidine salt include guanidine hydrochloride, guanidine thiocyanate (guanidine thiocyanate), guanidine sulfate, and guanidine isothiocyanate. Among them, guanidine hydrochloride or guanidine thiocyanate is preferable. These salts may be used solely or combined with each other.

In the mixture of the chaotropic agent, the support and the solution containing the nucleic acid, the concentration of the chaotropic agent may be 0.5 M or more and 8 M or less, preferably 1 M or more and 8 M or less, more preferably 2 M or more and 8 M or less, and most preferably 4 M or more and 7 M or less.

Step b) is a step of separating the support on which the nucleic acid(s) is/are adsorbed from the mixture mixed at step a). Examples of separation methods include a method of centrifuging the mixture obtained at step a), precipitating the support on which the nucleic acid(s) is/are adsorbed, and then removing the supernatant. Since the relative density of the support on which the nucleic acid(s) is/are adsorbed is higher than that of water, the precipitation can be carried out easily by the centrifugation. Conditions for the centrifugation may be 6000 G for 1 minute, and more preferably 10000 G for 1 minute. Examples of the other separation methods include a method of using an ultrafiltration membrane or a mesh. The mixture obtained at step a) is passed through the ultrafiltration membrane or mesh having a smaller pore diameter than the particle size of the support on which the nucleic acid(s) is/are adsorbed, to separate the support on which the nucleic acid(s) is/are adsorbed. Such an ultrafiltration membrane is available in a kit, and a centrifugal filter kit represented by Ultrafree (registered trademark) manufactured by Merck Ltd., or Nanosep (registered trademark) manufactured by Pall Corporation can be obtained for use.

As required, the following washing treatment may be further performed after the procedure of step b) because it is possible that body fluid sample-derived material other than the nucleic acid(s) of interest is adsorbed on the surface of the support after step a). For example, to isolate the nucleic acid(s) with higher purity, treatment such as washing or degradation may be performed. Specific examples thereof include various treatments such as washing with water to remove non-specifically adsorbed compounds, washing with a surfactant to remove non-specifically adsorbed proteins, washing with a non-ionic surfactant-containing solution to remove ions and low-molecular compounds, washing with an organic solvent to remove non-specifically adsorbed hydrophobic compounds, adding a protein-degrading enzyme to degrade non-specifically adsorbed proteins, adding an RNA-degrading enzyme to isolate only DNA, and adding an DNA-degrading enzyme to isolate only RNA. The washing treatment is represented as a washing process 1 in FIG. 1.

Step c) is the step of mixing the support separated at step b) with the solution containing the anionic surfactant.

The anionic surfactant is a generic term of a surfactant in which an atomic group exhibiting a surfactant activity is an anion, and is also referred to as an anionic surfactant. The anion forms a salt with a cation, which is a counter ion thereof. For example, it is possible to preferably use a lithium salt, a sodium salt, a potassium salt, an ammonium salt, an amine salt, and a hydroxyammonium salt (amino alcohol salt).

The anionic surfactant can be classified according to kinds of ionic functional groups, and is classified into carboxylic acid type, sulfonic acid type, sulfate ester type, phosphoric ester type, and the like. The carboxylic acid type, the sulfonic acid type, and the sulfate ester type anionic surfactants are preferable.

Specific examples of the carboxylic acid type anionic surfactant include caprylic acid salt, pelargonic acid salt, capric acid salt, lauric acid salt, myristic acid salt, pentadecylic acid salt, palmitic acid salt, palmitoleic acid salt, margaric acid salt, stearic acid salt, oleic acid salt, vaccenic acid salt, linoleic acid salt, linolenic acid salt, eleostearic acid salt, arachidic acid salt, behenic acid salt, lignoceric acid salt, cholic acid salt, N-decanoylsarcosine salt, and N-lauroyl-sarcosine salt. Among these, caprylic acid salt, pelargonic acid salt, capric acid salt, lauric acid salt, N-decanoylsarcosine salt, or a N-lauroylsarcosine salt is preferable. Preferable specific examples of these carboxylic acid salts include sodium caprylate, sodium pelargonate, sodium caprate, sodium laurate, sodium N-decanoyl sarcosinate, and sodium N-lauroyl sarcosinate.

Specific examples of the sulfonic acid type anionic surfactant include 1-nonane sulfonate salt, 1-decane sulfonate salt, 1-dodecane sulfonate salt, 1-octadecane sulfonate salt, 1-undecane sulfonate salt, sodium cumene sulfonate, octylbenzene sulfonate salt, dodecylbenzene sulfonate salt, 1-tetradecane sulfonate salt, 1-pentadecane sulfonate salt, naphthalene sulfonate salt, butylnaphthalene sulfonate salt, 1-hexadecane sulfonate salt, sulfosuccinic acid bis(2-ethylhexyl) ester salt, and 5-sulfoisophthalic acid dimethyl ester salt. Among these, octylbenzene sulfonate salt and dodecylbenzene sulfonate salt are preferable. Preferable specific examples of these sulfonate salts include sodium octylbenzene sulfonate, and sodium dodecylbenzene sulfonate. The dodecylbenzene sulfonic acid has types such as hard type, soft type and mixture type, and any of the types can be preferably used.

Specific examples of the sulfate ester-type anionic surfactant include octyl sulfate salt, decyl sulfate salt, dodecyl sulfate salt, tetradecyl sulfate salt, and hexadecyl sulfate salt. Among these, octyl sulfate salt, decyl sulfate salt and dodecyl sulfate salt are preferable. Preferable specific examples of these sulfate ester salt include sodium octyl sulfate, sodium decyl sulfate, and sodium dodecyl sulfate.

The anionic surfactant may contain an ether bond(s) in the alkyl side chain(s) of the above compound(s).

The surfactants listed above may be used solely or combined with each other for use.

The anionic surfactant is preferably 0.01 wt % or more and 2 wt % or less, more preferably 0.05 wt % or more and 2 wt % or less, still more preferably 0.075 wt % or more and 2 wt % or less, particularly preferably 0.075 wt % or more and 1.5 wt % or less, in a final concentration of the solution mixed at step c). The concentration of the anionic surfactant can be controlled by addition to water or a buffer.

As the solution containing the anionic surfactant, it is possible to use a solution in which the anionic surfactant is dissolved. Water, a neutral to alkaline aqueous solution or a buffer can be used as the solvent. The solution containing the anionic surfactant can be prepared also by forming a salt resulting from neutralization of a free form of the anionic surfactant. For example, the solution containing sodium dodecyl sulfate can be prepared by dissolving sodium dodecyl sulfate into a sodium hydroxide aqueous solution or a buffer containing sodium.

The anionic surfactant can be brought into contact with the support at any timing. After the preparation of the solution containing the anionic surfactant, the support may be added to be mixed, or the solution containing the anionic surfactant may be prepared while the support is added.

Specific examples of the method of mixing the support with the solution containing the anionic surfactant include dipping the support in the solution containing the anionic surfactant. After the dipping, the resulting solution can be left to stand or stirred. The stirring may be carried out by pipetting or mixing by inversion, or by using a device such as a mixer or vortex. The mixing time is not particularly limited, but may be about one minute. The mixing time may be more than one minute. The support may be packed in a column to allow the solution containing the nucleic acid to pass therethrough.

Step d) is the step of separating the support on which the nucleic acid is adsorbed from the mixture mixed at step c). The separation method can be performed under the same conditions and in the same method as in step b).

After the operation of step d), washing treatment may be carried out in the same method as in the washing step 1) as required, because it is possible that residual of the anionic surfactant used at step c) in the system may cause influence on the subsequent measurement system for the collected nucleic acid. The washing treatment is represented as the washing step 2 in FIG. 1.

Step e) is the step of adding the eluent to the nucleic acid-adsorbed support separated at step (d) and collecting the nucleic acid(s).

In the addition of the above eluent to collect the nucleic acid(s), it is possible to separate the support from the solution, which the nucleic acid(s) is eluted in, under the same conditions and in the same method as in step b).

The method of mixing the eluent with the support on which the nucleic acid(s) is adsorbed is not particularly limited. For example, the mixing may be carried out by pipetting or mixing by inversion, or by using the device such as mixer or vortex. The mixing time is not particularly limited, but may be about 5 minutes, or more than 5 minutes.

The collected nucleic acid(s) can be chemically modified as necessary. Examples of chemical modifications include, with regard to the nucleic acid termini, fluorescent dye modification, quencher modification, biotin modification, amination, carboxylation, maleinimidation, succinimidation, phosphorylation and dephosphorylation. Other examples include staining by an intercalator. These modifications may be introduced by chemical reaction, or may be introduced by enzyme reaction. The nucleic acid(s) can be quantified indirectly by introducing these modification groups before the above quantification and quantifying the modification groups introduced via chemical modification instead of quantifying the nucleic acid(s). Since this disclosure allows a nucleic acid(s) to be collected, and especially a short-chain nucleic acid(s) to be collected with a high yield, sensitive quantification is possible in the above quantification.

The support is produced by adsorbing a water-soluble neutral polymer onto the surface of aluminum oxide. The surface coverage ratio of the polymer is preferably 7% or more, more preferably 10% or more, further preferably 20% or more, particularly preferably 30% or more, and the most preferably 40% or more. The water-soluble neutral polymer may not be necessarily adsorbed in an even thickness.

In the support, the coverage ratio of the polymer on alumina is calculated by analyzing a potential map obtained from a surface potential microscope (also known as Kelvin probe force microscope; KFM). For the surface potential microscope, for example, NanoScope Iva AFM Dimension 3100 Stage AFM System manufactured by Digital Instruments of Bruker AXS can be used.

When the surface coverage ratio is calculated by use of the surface potential microscope, the measurement scale of the field of the view is within a range of 0.5 µm×1 µm. The surface coverage ratio is calculated as follows. First, the surface potential image of the aluminum oxide is obtained to calculate the average potential in the field of the view. Next, the surface potential image of the water-soluble neutral polymer is obtained to calculate the average potential in the field of the view. The surface potential image of the aluminum oxide on which the water-soluble neutral polymer is adsorbed is then obtained to calculate the average potential in the field of the view. The coverage ratio of the aluminum oxide alone is considered as 0% and that of the water-soluble neutral polymer alone is considered as 100%. The ratio of the average potential of the aluminum oxide on which the water-soluble neutral polymer is adsorbed to that of the water-soluble neutral polymer is obtained, and thus the surface coverage ratio of the aluminum oxide on which the water-soluble neutral polymer is adsorbed is calculated. When the surface coverage ratio is calculated, for the average potential in each field of view to be used, three single particles of the support are selected randomly, and each average value of measured values is used.

Photoshop manufactured by Adobe Systems Incorporated can be used as an image analysis software when the surface coverage ratio is calculated. In this instance, in the image analysis, the average value of the surface potential of the aluminum oxide is used as a lower limit of the scale, and the average value of the surface potential of the water-soluble neutral polymer is used as an upper limit of the scale. The lower limit color is set with black (8 bits, RGB value 0), and the upper limit color is set with red (R value 255), green (G value 255), blue (B value 255), or the like. The surface potential image of the aluminum oxide on which the water-soluble neutral polymer is adsorbed is displayed in the scale set as above, and either the R value, the G value, or the B value is divided by 255, and the ratio is used as the surface coverage ratio.

Before the water-soluble neutral polymer is adsorbed on the surface, the aluminum oxide may be washed in advance with a solution such as water or ethanol to remove the impurities adsorbed on the surface, or this washing step may be omitted.

Examples of methods for adsorbing the water-soluble neutral polymer on the surface of the aluminum oxide include a method of dissolving the water-soluble neutral polymer to prepare a water-soluble neutral polymer solution and bringing the solution into the contact with the aluminum oxide. Specifically, the aluminum oxide may be dipped in the water-soluble neutral polymer solution, the water-soluble neutral polymer solution may be added dropwise to the aluminum oxide, the water-soluble neutral polymer solution may be coated on the aluminum oxide, the water-soluble neutral polymer solution may be sprayed onto the aluminum oxide in the form of a mist.

The methods of dipping the aluminum oxide in the water-soluble neutral polymer solution are not particularly limited. For example, it may be stirred by pipetting or mixing by inversion, or by a disperser such as a stirrer, mixer, vortex or a mill, a sonication instrument, or the like.

The concentration of the water-soluble neutral polymer is not particularly limited, but preferably 0.01 wt % or more, and more preferably 0.1 wt % or more.

The mixing time for stirring is not particularly limited as long as the water-soluble neutral polymer and the aluminum oxide are mixed evenly, but in a vortex, it is stirred for 1 minute or more, and preferably 5 minutes or more.

The water-soluble neutral polymer can also be dip-coated on the aluminum oxide using a sifter, a sieve, or the like. The mixing time for dipping in the solution may be, in the example of the polymer concentration of 0.1 wt % or more, 5 minutes or more, and preferably 30 minutes or more.

When the water-soluble neutral polymer solution is added dropwise, a dropper, a dropping funnel, or the like can be used. When the polymer solution is added dropwise, the aluminum oxide may also be shaken or rotated, or a spin coater or the like may be used.

When the water-soluble neutral polymer solution is coated, a brush, roller or a wire bar can be used.

When the water-soluble neutral polymer solution is sprayed in a form of a mist, an air spray, an air brush, or the like can be used.

After the water-soluble neutral polymer is adsorbed on the aluminum oxide in the methods described above, a centrifugation may be carried out to remove the supernatant polymer solution, or the aluminum oxide is directly used for nucleic acid collection without centrifugation. When the polymer solution is dissolved in a solvent, after the water-soluble neutral polymer is adsorbed on the aluminum oxide and the solvent is removed, it may be dried or may be used directly for collecting a nucleic acid(s) without drying.

The support may be preserved for use after prepared in advance, or prepared at time of use.

When the obtained water-soluble neutral polymer is solid, the water-soluble neutral polymer solution can be prepared by dissolving the polymer in water or an organic solvent, and when the obtained water-soluble neutral polymer is a solution, the water-soluble neutral polymer solution may be prepared by diluting the solution. When it is hard to dissolve the polymer or mix the polymer due to the high viscosity of the solution, a heating treatment or sonication may be performed. Examples of organic solvent include ethanol, acetonitrile, methanol, propanol, tert-butanol, DMF, DMSO, acetone, ethylene glycol and glycerol. It is preferred that solvents compatible with water are used. When the polymer is poorly soluble in water, any of the above organic solvents may be added.

A support produced by binding covalently the aluminum oxide and the water-soluble neutral polymer by, for example, a linker molecule is not the support. Specific examples of linker molecules include silane coupling agents. A support, which is prepared by forming amido bond(s), ester bond(s), Michael addition product with thiol and maleimide, disulfide bond(s), triazole ring(s) and then immobilizing polymer and the like, is also not the support.

The kit that collects the nucleic acid(s) can be used to collect the nucleic acid(s) from a body fluid sample efficiently. The kit may include the aluminum oxide support with the water-soluble neutral polymer adsorbed on the surface thereof, the solution containing the chaotropic agent and the solution containing the anionic surfactant as its constituent components, and may include a buffer solution. The kit may further include specifications and instructions of the kit in addition to these components.

The kit may contain the aluminum oxide support with the water-soluble neutral polymer adsorbed on the surface thereof. The aluminum oxide support may be kept in a dry condition, or dipped in a solution of a water-soluble neutral polymer.

As the buffer solution included in the kit, a buffer solution which can be used as the eluent in the above step e) may be utilized.

For the body fluid sample, any body fluid sample containing a nucleic acid(s) can be used. Examples of the nucleic acids include RNA, DNA, RNA/DNA (chimera) and artificial nucleic acids. Examples of DNA include cDNA, micro DNA (miDNA), genome DNA, synthetic DNA, cell-free DNA (cfDNA), ctDNA, mitochondrial DNA (mtDNA). Examples of RNA include total RNA, mRNA, rRNA, miRNA, siRNA, snoRNA, snRNA or non-coding RNA, precursors thereof, and synthetic RNA. Synthetic DNA and synthetic RNA can be produced artificially based on a predetermined base sequence (it may be either native sequence or non-natural sequence) by use of, for example, an automated nucleic acid synthesizer.

As the body fluid sample, for example, body fluids such as blood, urine, saliva, mucous membrane, sweat, sputum, and semen can be used. The body fluid sample is preferably blood, urine, and saliva. Examples of blood include whole blood, plasma, serum, and blood cells.

The body fluid sample may be used as it is after collected to be utilized or diluted with a solution after the collected. When containing precipitants and floating materials in large amounts, body fluid sample may be centrifuged to form a pellet thereof and use a supernatant only. The body fluid sample may be filtered with a filter. The supernatant and the filtered body fluid sample may be diluted with water or the buffer solution before being used.

The body fluid sample may be subjected to a treatment as explained below if necessary. The treatment is carried out because the nucleic acid(s) in the biological sample containing the body fluid is often capsuled in a compound such as a cell membrane, a cell wall, a vesicle, a liposome, a micelle, a ribosome, a histone, a nuclear membrane, a mitochondrion, a virus capsid, an envelope, an endosome, an exosome and the like, and because they often interact with each other. To collect the nucleic acid(s) with a better yield, a treatment to release the nucleic acid(s) from such materials may be carried out.

Specifically, the following treatment may be performed to improve the collection efficiency of the nucleic acid(s) from the body fluid sample containing *E. coli*. For example, a mixture solution of 0.2 M of sodium hydroxide and 1% sodium dodecyl sulfate (SDS) may be added to the body fluid sample containing *E. coli* (alkaline denaturation method), or a 10% sarkosyl solution may be added to the body fluid sample containing *E. coli* (non-denaturation method by sarkosyl). Lysozyme may be added to these solutions. The sample may also be treated with proteinase K at 37° C. for one hour. Other methods also include a sonication.

To improve the collection efficiency of the nucleic acid(s) from a yeast-containing body fluid sample, the following treatment may be performed on the body fluid sample. For example, the body fluid sample may be treated with zymolyase commercially available from Seikagaku Corporation, and then 10% SDS may be added.

To improve the collection efficiency of the nucleic acid(s) from a cell-containing body fluid sample, the following treatment may be performed on the body fluid sample. For example, 1% SDS or TritonX may be added. Other methods include adding guanidinium chloride, a guanidine thiocyanate salt, urea or the like in a final concentration of 4 M or more. Sarkosyl may be added to this solution in a concentration of 0.5% or more. Mercaptoethanol may also be added to result in a concentration of 50 mM or more.

In the above procedures, an inhibitor of a degradative enzyme of the nucleic acid(s) may be added to suppress the degradation of the nucleic acid(s) contained in the body fluid sample. As the inhibitor of DNA-degrading enzymes, EDTA may be added in a concentration of 1 mM or less. It is possible to use commercially available inhibitors of RNA-degrading enzymes such as RNasin Plus Ribonuclease Inhibitor (Promega Corporation), Ribonuclease Inhibitor (TAKARA BIO INC.), and RNase inhibitor (Toyobo Co., Ltd.).

When DNA and RNA coexist in the body fluid sample, they can be separated by phenol-chloroform extraction. For example, when the phenol-chloroform extraction is performed under acidic conditions, RNA and DNA are separated into a water layer and a chloroform layer, respectively. Under the neutral conditions, RNA and DNA are distributed into a water phase. This nature can be utilized to select the conditions depending on the type of the desired nucleic acid(s). The above-mentioned chloroform may be replaced by p-bromoanisole.

In the phenol-chloroform extraction, it is also possible to use a commercially available reagent, ISOGEN (registered trademark) (Nippon Gene Co., Ltd.), TRIzol (registered trademark) (Life Technologies Japan Ltd.), RNAiso (Takara Bio Inc.), or 3D-Gene (registered trademark) RNA extraction reagent from liquid sample kit (Toray Industries, Inc.). A single step in the treatments described above can be performed alone, or combined with another step(s) of a different procedure(s). The concentration of the solution to be used may be changed as required.

The body fluid sample or a diluted solution thereof can be used as the solution containing the nucleic acid(s). It is also possible to use a solution prepared by mixing the body fluid sample with a solution in which the nucleic acid(s), an artificial nucleic acid(s), or a nucleic acid(s) modified with a dye or a phosphoric group(s) is dissolved. For the body fluid sample, it is possible to use the solution resulting from the above treatment as it is, or dilute the resulting solution as required. The solution to be used for the dilution is not particularly limited, but preferably a solution that is widely used with the solution containing the nucleic acid(s) such as water, a HEPES buffer solution or a Tris-hydrochloric acid buffer solution.

The length of the nucleic acid(s) to be collected is not particularly limited, but preferably 1000 base pairs or less. Furthermore, our methods enable high yield collection of the nucleic acids of 300 base pairs or less such as cell-free DNA and ctDNA, which were difficult to collect in the prior arts, as well as high yield collection of pre-miRNAs and miRNAs of 100 base pairs or less.

The collection yield of the nucleic acid(s) can be measured in the following way. Examples of methods of quantifying the amount of the nucleic acid(s) include a UV-vis absorbance measurement, a fluorescence measurement, a luminescence measurement, electrophoresis, PCR, RT-PCR, an analysis using a microarray, and an analysis using a sequencer. For the unmodified nucleic acid(s), the amount of the nucleic acid can be quantified by the measurement of absorbance at 260 nm. For the nucleic acid(s) modified with a fluorescent dye, the amount of the nucleic acid can be quantified by comparing the fluorescence intensity derived from the fluorescent dye with the fluorescence intensity of a solution with a known concentration. The quantification is carried out also by electrophoresis. As the calculation method of the collection ratio by electrophoresis, it is possible to determine the collection ratio by carrying out the electrophoresis for the sample with known concentration and the sample obtained by the collection procedure simultaneously, staining the gel, and then comparing concentration of the resulting bands by the image analysis.

When the amount of the nucleic acid(s) is too small to be quantified, the yield of the nucleic acid(s) can be compared by using a method such as DNA chip and real-time PCR to detect nucleic acid(s) and then comparing the detected values. For example, in a reaction for detecting with use of DNA chip or the like, higher signal value can be interpreted as a higher yield in the measurement system based on fluorescence measurement and luminescence measurement. For example, in the DNA chip, the yield can be compared by acquiring a fluorescent image with a scanner, and quantifying fluorescence signal intensities for the genes. For comprehensive analysis of an expression level of miRNA, mRNA or the like, it is possible to compare the fluorescence signal intensities for the genes and interpret a higher signal value as a higher yield by the comparison with a different way. Multiple types of gene can be analyzed by taking a summation of fluorescence signals of genes (fluorescence signal total value) to interpret a higher signal value as a higher yield by the comparison with a different way. In the real-time PCR, it is possible to obtain an amplification curve by plotting with a horizontal axis representing number of cycles and a vertical axis representing fluorescence intensity, and then determine the number of cycles (Cq value and Ct value) reaching to a predetermined signal intensity in this amplification curve. In this instance, smaller Ct value or Cq value can be interpreted as a higher yield. In cfDNA and genome DNA, primer for the gene to be measured is designed, it is possible to interpret a smaller Cq value or Ct value as a higher yield by the comparison with a different collection method for the same primer. In RNA such as miRNA or mRNA, it is possible to measure and detect in the same way as DNA except for adding a step of reverse transcription, and interpret smaller Ct value or Cq value as a higher yield.

Polymer is a general term representing a compound that is formed by linking multiple repeating units, each of which is referred to as a monomer serving as a basic unit. The polymers to be used in the support include both of homopolymer(s) consisting of one monomer and copolymer(s) composed of two or more monomers as well as polymers with arbitrary degrees of polymerization and both of naturally occurring polymers and synthetic polymers.

The water-soluble neutral polymer used in the support is a polymer with water-soluble property. The solubility in water is at least 0.0001 wt % or more, preferably 0.001 wt % or more, more preferably 0.01 wt % or more, and further preferably 0.1 wt % or more.

The water-soluble neutral polymer used in the support is a polymer having a zeta potential of not less than −10 mV and not more than +10 mV in a solution of pH 7. More preferably, the water-soluble neutral polymer used in the support is a polymer having a zeta potential of not less than −8 mV and not more than +8 mV, further preferably not less than −6 mV and not more than +6 mV, and particularly preferably not less than −4.0 mV and not more than +1.1 mV.

The zeta potential is one of values indicating electrical properties on colloidal interfaces in a solution. When charged colloids are dispersed in a solution, on the surface of a colloid, an electrical double layer is formed by counter ions with respect to the charge of the colloidal surface. The electrical potential on this colloidal surface is called surface potential. Because the electrical double layer is formed by electrostatic interaction between the colloidal surface charges, ions are more strongly fixed as they are closer toward the colloid. In the electrical double layer, a layer in which counter ions are strongly fixed on the colloidal surface by electrostatic interaction is called a stern layer, and the potential of the stern layer is called a fixed potential. When a colloid is moved relative to a solution, the stern layer is also moved together with the colloid. In this example, there is a boundary surface that is moved together with the colloid outside the stern layer as viewed from the colloid due to the viscosity of the solution. This surface is called a slipping plane. The potential of this slipping plane is defined as a zeta potential when the potential at a point sufficiently far from the colloid is defined as zero. Thus, as the zeta potential varies depending on the colloidal surface charge and the surface charge changes according to protonation and deprotonation which depend on pH, the value in a solution of pH 7 is used as a standard. Because the distance from the colloidal surface to the slipping plane is generally small compared to the colloidal size, the colloidal surface can be represented approximately as the slipping plane. In the water-soluble neutral polymer as well, the colloidal surface potential dispersed in the solution can be considered as the zeta potential.

The zeta potential can be obtained by use of electrokinetic phenomenon such as electrophoresis, electro-osmosis, back flow potential, and sedimentation potential, and can be measured by a method such as a microscopic electrophoresis method, an electrophoresis method using a rotating diffraction grating method, a laser Doppler electrophoresis method, an ultrasonic vibration potential method, and an electroacoustic method. These measurements can be performed using a zeta potential measurement instrument. The zeta potential measurement instruments are commercially available from, for example, Otsuka Electronics Co., Ltd., Malvern Instruments Ltd., Ranku Brother Ltd., and PenKem Inc.

Any of the above instruments can be used to measure the zeta potential, but the laser Doppler electrophoresis method is common. The laser Doppler electrophoresis method is a measurement method that utilizes the Doppler effect. The Doppler effect causes the change in the frequency of light or sound waves when the light or sound waves strike an object in motion due to electrophoresis, and scatter or reflect.

When the zeta potential of a polymer is measured, a polymer solution can be prepared as a colloid dispersion to measure the zeta potential. For example, a polymer is dissolved in an electrolyte such as a phosphate buffer solution, a sodium chloride solution, and a citrate buffer solution to form a polymer solution, and scattered light and reflected light of the polymer scattered in the solution are detected for the measurement. A bigger colloid size allows for the detection of scattered light and reflected light under a lower concentration.

Specific conditions for measuring the zeta potential of a polymer by the laser Doppler method is not particularly limited, but the zeta potential of the polymer can be measured as follows, for example: the polymer is dissolved in a phosphate buffer solution (10 mM, pH 7) under the concentration of not less than 1 wt % and not more than 10 wt %; this solution is then placed in a cell for measurement and installed in a zeta potential measurement instrument which utilizes the principle of the laser Doppler electrophoresis method, and thus the zeta potential can be measured at room temperature. As the zeta potential measurement instrument, for example, ELS-Z manufactured by Otsuka Electronics Co., Ltd., can be used.

Examples of the water-soluble neutral polymer used in the support include the following. For example, a polyvinyl polymer such as polyvinyl alcohol or polyvinylpyrrolidone, a polyacrylamide polymer such as polyacrylamide, poly(N-isopropylacrylamide) or poly(N-(hydroxymethyl)acrylamide, a polyalkylene glycol polymer such as polyethylene glycol, polypropylene glycol, or polytetramethylene ether glycol, or a cellulose such as poly(2-ethyl-2-oxazoline), (hydroxypropyl)methyl cellulose, methyl cellulose, ethyl cellulose, 2-hydroxyethyl cellulose, or hydroxypropyl cellulose or the like can be used. Copolymers containing the above polymer can be also used.

Other examples of the water-soluble neutral polymer used in the support also include polysaccharides or polysaccharide analogs such as ficoll, agarose, chitin and dextran as well as proteins and peptides such as albumin.

A part of a functional group of the water-soluble neutral polymer may be ionized or substituted with a functional group illustrating positivity or negativity. A functional group exhibiting solubility in water such as an acetyl group may be introduced to side chains.

The molecular weight of the water-soluble neutral polymer is, for example, preferably 0.4 kD or more, and more preferably, 6 kD or more.

The aluminum oxide used in the support is an amphoteric oxide expressed by the composition formula, $Al_2O_3$ and is also known as alumina.

For the aluminum oxide, naturally produced aluminum oxide or aluminum oxide manufactured industrially may be used. Examples of methods for producing aluminum oxide include the Bayer method in which gibbsite is used as a starting material, an alkoxide method via a hydroxide in the form of boehmite (also called sol-gel method), a neutralization method, an oil droplet method, an aluminum salt thermal decomposition method, and an anodic oxidation method.

Aluminum oxide manufactured industrially can be available from reagent manufacturers, catalyst chemical manufacturers, the Committee of Reference Catalyst of the Catalysis Society of Japan and the like.

Depending on the crystal structure, aluminum oxide is classified as alpha aluminum oxide, rho aluminum oxide, khi aluminum oxide, kappa aluminum oxide, eta aluminum oxide, gamma aluminum oxide, delta aluminum oxide, theta aluminum oxide, or the like. Gamma aluminum oxide with a high specific surface area is preferred.

Aluminum oxide changes its acid sites ($Al^+$, $Al—OH_2^+$) and basic sites ($Al—O^-$) depending on the calcination temperature during the production. Depending on the number of acid sites and basic sites of the aluminum oxide, the aluminum oxide is classified as acidic alumina if there are more acid sites, as basic alumina if there are more basic sites, and as neutral alumina if the acid sites and the basic sites are almost equal. The difference in this property can be confirmed by the addition of a pH indicator, i.e., BTB solution. When a BTB solution is added, if the aluminum oxide turns yellow, the aluminum oxide is acidic alumina; if the aluminum oxide turns green, it is neutral alumina; and if the aluminum oxide turns blue, it is basic alumina. Any aluminum oxide can be used regardless of such a difference in property.

Aluminum oxide is preferably in a granular form. The particle size may be the same, or different particle sizes can be combined in use. For example, the aluminum oxide having a particle size of less than 212 μm can be preferably used, more preferably the aluminum oxide having a particle size of less than 100 μm can be used.

The particle size is defined by an aperture size of a sieve based on JIS Z-8801-1:2006 according to Japanese Industrial Standards. For example, in the aperture size according to the above JIS standard, particles which can pass through the sieve of 40 μm and cannot pass through the sieve of 32 μm will have the particle size of not less than 32 μm and less than 40 μm.

The eluent used at step e) is not particularly limited as long as the nucleic acid(s) adsorbed on the support can be eluted, but is preferably a buffer solution, and the buffer solution may contain a chelating agent. Specific examples thereof include a citrate buffer solution containing citric acid and sodium citrate, a phosphate buffer solution containing phosphoric acid and sodium phosphate, and a Tris-EDTA buffer solution obtained by adding EDTA to a Tris-hydrochloric acid buffer solution containing tris hydroxy aminomethane and hydrochloric acid.

The pH of the buffer solution is preferably pH 4 or more and pH 9 or less, and more preferably pH 5 or more and pH 8 or less.

Water and the buffer solution can be used as the eluent used at step e), and the buffer solution is preferable.

Examples of the buffer solution preferably used are a phosphate buffer solution containing phosphoric acid and sodium phosphate, a citric acid buffer solution containing citric acid and sodium citrate, and a tris-EDTA buffer solution obtained by adding EDTA to a tris-hydrochloric acid buffer solution containing tris-hydroxyaminomethane and hydrochloric acid. Among these, the citric acid buffer solution containing citric acid and sodium citrate, and the tris-EDTA buffer solution obtained by adding EDTA to the tris-hydrochloric acid buffer solution containing tris-hydroxyaminomethane and hydrochloric acid have chelating functions and are particularly preferable. The pH of the buffer solution is preferably pH 4 or more and pH 9 or less, and more preferably pH 5 or more and pH 8 or less.

A chelating agent may be added to the buffer solution to add the chelating function to the buffer solution. The chelating agent has a ligand with plural coordination sites, and can be bound to a metal ion to form a complex. The buffer solution containing the chelating agent has the chelating function Specific examples of chelating agents to be added to the buffer solution include ethylenediaminetetraacetic acid (EDTA), nitrilotriacetic acid (NTA), glycol ether diamine tetraacetic acid (EGTA), phosphoric acid, polyphosphoric acid, triphosphoric acid, metaphosphoric acid, phytic acid and/or and salts thereof. The final concentration of the chelating agent is preferably 50 mM or more, and is more preferably 100 mM or more, and further preferably 500 mM or more.

Examples of compounds as a chelating agent other than the above include anionic polymers. Since a polymer which has carboxylic acid on the side chains coordinate to a metal ion, the buffer solution may contain such a polymer. Examples of polymers having such a function include polyvinyl sulfonic acid and/or salt thereof. The final concentration is not particularly limited as long as it is 1 wt % or more, and preferably 10 wt % or more.

The above chelating agents can be used solely or mixed with each other for use. It is preferable to use phosphoric acid-polyphosphate mixture, phosphoric acid-triphosphoric acid mixture, phosphoric acid-metaphosphoric acid mixture, or phosphoric acid-phytic acid mixture.

EXAMPLES

Our methods are described more specifically with reference to Examples described below.

Material and Method

Polyethylene glycol was purchased from Merck Ltd. Gamma aluminum oxide (N613N) was purchased from JGC Catalysts and Chemicals Ltd. A 10% solution of sodium dodecyl sulfate (SDS) was purchased from Invitrogen Corporation. Sodium dodecylbenzene sulfonate, sodium Laurate, sodium N-Lauroylsarcosinate were purchased from Tokyo Chemical Industry Co., Ltd.

Other agents were purchased from Wako Pure Chemical Industries, Ltd., Tokyo Chemical Industry Co., Ltd., and Sigma-Aldrich Japan, and used directly without any particular purification.

CUTE MIXER CM-1000 manufactured by Tokyo Rikakikai Co., Ltd. was used as a mixer. CT15RE manufactured by Hitachi, Ltd. was used as a centrifuge.

Human serum and human blood plasma were collected from healthy persons who obtained informed consent, with use of Venoject II vacutainer blood collection tubes VP-AS109K60 (Terumo Corporation).

The support was prepared to be utilized in Examples and Comparative Examples described below by the following way: weighting out 0.5 mg of aluminum oxide and adding it to a 1.5 mL tube; adding 50 µL of polyethylene glycol (PEG, 10 kD) with a 10 wt % concentration as a water-soluble neutral polymer to the tube; string the resulting solution with the mixer for 10 minutes; centrifuging (at 10000 G for 1 min); and then removing the 45 µL of supernatant to obtain an aluminum oxide support with water-soluble neutral polymer adsorbed on a surface thereof.

Examples 1 and 2

Sodium dodecyl sulfate (SDS) was used as an anionic surfactant to collect a nucleic acid(s). Experimental method for each step is described below.

Step a)
7 M guanidine thiocyanate (GTN) was used as a chaotropic agent. Human serum was used as a solution containing the nucleic acid. The above prepared aluminum oxide support was mixed with 7 M GTN, 450 µL of 25 mM HEPES (pH 7) solution and 100 µL of human serum. The resulting solution was stirred with the mixer for 15 minutes.

Step b)
The solution mixed at step a) was centrifuged (at 10000 G for 1 min) to remove the supernatant to separate the aluminum oxide support on which the nucleic acids is adsorbed.

Washing Step 1
400 µL of 25 mM HEPES aqueous solution (pH 7) (Example 1) or 0.05% Tween20 aqueous solution (Example 2) was added to the nucleic acid-adsorbed support obtained at step b) and then vortexed. The resulting solution was centrifuged (at 10,000 g for 1 min) to remove the supernatant for separating the support.

Step c)
400 µL of 25 mM HEPES (pH 7) containing 0.5% SDS was added to the separated support as the solution containing the anionic surfactant.

Step d)
The solution mixed at step c) was centrifuged (at 10000 G for 1 min) to discard the supernatant for separating the support on which the nucleic acids are adsorbed.

Washing Step 2
400 µL of 25 mM HEPES aqueous solution (pH 7) (Example 1) or 0.05% Tween20 aqueous solution (Example 2) was added to the nucleic acid-adsorbed support obtained at step d) and then vortexed. The resulting solution was centrifuged (at 10000 G for 1 min) to remove the supernatant for separating the support.

Step e)
To the separated support, 10 µL of 125 mM phosphoric acid-125 mM polyphosphate buffer (pH 7) was added as an eluent. The resulting solution was stirred with the mixer for 15 minutes. Next, the stirred solution was centrifuged (at 10000 G for 1 min) for the collection of the supernatant as a nucleic acid solution.

Measurement of Amount of Collected Nucleic Acid (Fluorescence Signal Total Value)

For the nucleic acid collected from the serum through the above steps, miRNA was fluorescence-labeled using a 3D-Gene (registered trademark) miRNA Labelling kit (Toray Industries, Inc.) according to the protocol established by Toray Industries, Inc. As an oligo DNA chip, 3D-Gene (registered trademark) Human miRNA Oligo chip (Toray Industries, Inc.), in which a probe with a complementary sequence to 2565 species of miRNA is mounted, was selected for use, among miRNAs registered in miRBase release 21. Hybridization and washing after the hybridization were carried out under stringent condition according to the protocol established by Toray Industries, Inc. The DNA chip was scanned with a 3D-Gene (registered trademark) scanner (Toray Industries, Inc.) to acquire an image. Then, fluorescence signal intensities of amounts of miRNAs were quantified using 3D-Gene (registered trademark) Extraction (Toray Industries, Inc.). The quantified fluorescence signal intensities were divided by Planck value to obtain S/N value. The summation was taken for all fluorescence signal intensities with the S/N value of 1.5 or more (Fluorescence signal total value). Results of Examples 1 and 2 are listed in Table 1.

Example 3

The nucleic acids were collected in the collection steps of Example 1 except that the washing step 1 was omitted. The other conditions and operations were carried out in the same manner as in Example 1. The summation was taken for all fluorescence intensities of miRNA in blood using the DNA chip. Results are listed in Table 1.

These results demonstrate that the nucleic acids can be collected to the same extent as in Example 1, even that the nucleic acid was collected at the steps except for the washing step 1.

Comparative Examples 1 and 2

In comparative examples 1 and 2, the other conditions and operations were carried out to collect the nucleic acid under the same conditions and by the same operation as in Examples 1 and 2, except that steps c) and d) were omitted. That is, the Comparative Examples correspond to a method of collecting the nucleic acid described in WO '763. Results are listed in Table 1.

The results of Examples 1 and 2 and Comparative Examples 1 and 2 demonstrate that Examples 1 and 2 including step c) of adding anionic surfactant improve the fluorescence signal total value and increase the amount of collected nucleic acid compared with the method of Comparative Examples 1 and 2, namely, WO '763.

TABLE 1

|  | Washing step 1 | Step c) Anionic surfactant | Washing step 2 | Fluorescence signal total value |
|---|---|---|---|---|
| Example 1 | HEPES | 0.5% SDS | HEPES | 237837 |
| Example 2 | Tween20 | 0.5% SDS | Tween20 | 258048 |
| Example 3 | None | 0.5% SDS | HEPES | 199573 |
| Comparative Example 1 | HEPES | None | HEPES | 64848 |
| Comparative Example 2 | Tween20 | None | Tween20 | 62075 |

Comparative Example 3

The nucleic acid was collected without the use of a chaotropic agent at step a) of Example 1. At step a), a mixture of 100 μL of human serum and 450 μL of 25 mM HEPES (pH 7) solution was used as the solution containing the nucleic acid. The other conditions and operations were carried out in the same manner as in Example 1. The summation was taken for all fluorescence intensities of miRNA in blood using the DNA chip. Results are listed in Table 2.

These results demonstrate that the absence of the chaotropic agent at step a) causes low amount of collected nucleic acid from the body fluid and low fluorescence signal total value even when step c) was performed.

Comparative Example 4

When the body fluid contains E. coli, yeast, cells, and the like, the free treatment of the nucleic acid may be carried out to enhance the collection efficiency of the nucleic acid. Thus, the anionic surfactant such as SDS is contained in the solution containing the nucleic acid. The nucleic acid was collected in the following way, with use of the anionic surfactant at step a) and the chaotropic agent at step c).

At step a) of the collection steps of Example 1, 0.5% SDS, 25 mM HEPES (pH 7) was used instead of 7 M guanidine thiocyanate (GTN). At step c), 7 M guanidine thiocyanate (GTN) and 25 mM HEPES (pH 7) were used instead of 0.5% SDS, 25 mM HEPES (pH 7). The other conditions and operations were carried out in the same manner as in Example 1. The summation was taken for all fluorescence intensities of miRNA in blood using the DNA chip. Results are listed in Table 2.

According to these results, the improvement of the nucleic acid collection amount and the total value of fluorescence intensity is not confirmed when the process does not include adsorbing the nucleic acid on the support in the presence of a chaotropic agent and the method of adding the anionic surfactant after the adsorbing the nucleic acid on the support.

Comparative Example 5

The nucleic acid was adsorbed on the support by using both the chaotropic agent and the anionic surfactant at step a) of Example 1, and collected without steps c) and d) being carried out. A solution obtained by mixing 7M guanidine thiocyanate (GTN) with 0.5% SDS, 25 mM HEPES (pH 7) was used at step a). The other conditions and operations were carried out in the same manner as in Comparative Example 1. Results are listed in Table 2.

According to these results, the process not including steps c) and d) resulted in a low amount of nucleic acid collected from the body fluid sample and low fluorescence signal total value even when the anionic surfactant was added at step a).

TABLE 2

|  | Step a) Chaotropic agent | Step c) Anionic surfactant | Fluorescence signal total value |
|---|---|---|---|
| Comparative Example 3 | None | 0.5% SDS | 70712 |
| Comparative Example 4 | (No chaotropic agent) 0.5% SDS | (No anionic surfactant) 7M GTN | 22207 |
| Comparative Example 5 | 7M GTN, 0.5% SDS | None | 60761 |

Examples 4, 5, and 6

0.5% SDS of step c) in Example 1 was substituted with 0.5% sodium dodecylbenzene sulfonate (Example 4), 0.5% N-lauroyl sarcosinate (Example 5) or 0.25% sodium laurate (Example 6). The other conditions and operations were carried out in the same manner as in Example 1 to collect the nucleic acids. Results are listed in Table 3.

These results demonstrate that the use of various anionic surfactants at step c) leads to increase in the amount of nucleic acid and improvement of the fluorescence signal total value.

TABLE 3

|  | Step c) Anionic surfactant | Fluorescence signal total value |
|---|---|---|
| Example 4 | 0.5% Sodium dodecylbenzene sulfonate | 135991 |
| Example 5 | 0.5% Sodium N-Lauroyl sarcosinate | 150848 |
| Example 6 | 0.25% Sodium laurate | 112323 |

Examples 7, 8, and 9

The SDS concentration at step c) in Example 1 was controlled to 1% (Example 7), 0.1% (Example 8), or 0.075% (Example 9). The nucleic acid was collected by the same operations under the same conditions as Example 1. Results are listed in Table 4.

These results demonstrate that the amount of collected nucleic acid is increased and the fluorescence signal total value is improved at any concentration of the anionic surfactant.

TABLE 4

|  | Step c) Anionic surfactant | Fluorescence signal total value |
|---|---|---|
| Example 7 | 1% SDS | 196026 |
| Example 8 | 0.1% SDS | 111781 |
| Example 9 | 0.075% SDS | 104961 |

Examples 10 and 11

7M guanidine hydrochloride (Example 10) or 8 M urea (Example 11) was used instead of the 7M guanidine thiocyanate at step a) in Example 1. The other conditions and operations were carried out in the same manner as in Example 1 to collect the nucleic acids. Results are listed in Table 5.

From these results, we found that the use of various chaotropic agents at step a) leads to increase in the amount of nucleic acid collected from the body fluid and improvement of the fluorescence signal total value.

TABLE 5

|  | Step a) Chaotropic agent | Fluorescence signal total value |
|---|---|---|
| Example 10 | 7M GH | 157517 |
| Example 11 | 8M Urea | 135348 |

Examples 12, 13, 14, and 15

The concentration of guanidine thiocyanate that was used as the chaotropic agent at step a) in Example 1 was controlled to 4 M (Example 12), 2 M (Example 13), 1 M (Example 14) and 0.5 M (Example 15). The other conditions and operations were carried out in the same manner as in Example 1 to collect the nucleic acids. Results are listed in Table 6.

From these results, we found that the amount of nucleic acid collected from the body fluid is increased and the fluorescence signal total value is improved in any of the concentrations of the chaotropic agent.

TABLE 6

|  | Step a) Chaotropic agent | Fluorescence signal total value |
|---|---|---|
| Example 12 | 4M GTN | 178474 |
| Example 13 | 2M GTN | 143263 |
| Example 14 | 1M GTN | 101124 |
| Example 15 | 0.5M GTN | 87999 |

Example 16

The other conditions and operations were carried out to collect the nucleic acids under the same conditions and by the same operation as in Example 2 except that: 300 µL of plasma was used as the body fluid sample; 450 µL of 7M guanidine thiocyanate (GTN) was used as the chaotropic agent; and 50 µL of 0.5 M phosphate buffer solution (pH 7) was used as an eluent. Subsequently, confirmation was carried out in the following way as to whether cell-free DNA was contained in the collected nucleic acid.

As a means of confirming whether the cell-free DNA was collected, a method of measuring for nucleic acids with parts of gene sequence encoding actin-β of cell-free DNAs contained in plasma by using real-time PCR (W. Sun et al., The role of plasma cell-free DNA detection in predicting preoperative chemoradiotherapy response in rectal cancer patients. ONCOLOGY REPORTS 31: 1466-1472, 2014), is known. In this Example, on the basis of a method of detecting cell-free DNA by amplifying a gene sequence of 100 bp among the genes encoding actin-β described in this document, primers 1 and 2 for amplifying a nucleotide sequence with 93 bp among the gene sequence encoding actin-β are designed and used for measurement by real-time PCR.

In real-time PCR measurement, SYBR (registered trademark) Premix Ex Taq II manufactured by Takara Bio Inc. and CFX96-Real Time System manufactured by Bio-rad Laboratories, Inc., were used. A nucleic acid with 93 bp out of a gene sequence encoding actin-β was amplified and analyzed as an amplification cycle number (CQ value). As primers to amplify the nucleic acid, on the basis of description in Prime PCR assays, Panels, and Controls Instruction Manual (Bio-Rad Laboratories, Inc.), nucleic acids represented by sequence numbers 1 and 2 are designed, purchased from Euro Corporation Ltd., and used as they are without further purification.

First, 12.5 µL of SYBR Premix Ex Taq, 1.0 µL of the primer represented by sequence numbers 1 and 2 controlled to have a 0.5 µL concentration, 8.5 µL of sterile distilled water, and 2 µL of the sample of the nucleic acid collected in this Example that was 10-fold diluted with sterile distilled water, were mixed together inside a 1.5 mL tube placed on ice to prepare a solution with a total volume of 25 µL. The total volume of the solution was added to a real-time PCR plate, covered with a plate sheet, and then placed on the instrument. Measurement condition of the real-time PCR is: separating double-stranded DNA into a single-stranded DNA at 95° c. for 30 seconds; annealing the primer at 95° c. for 5 seconds; and performing elongation reaction in 40 cycles. Each cycle was performed at 56° c. for one minute. An amplification cycle number was obtained from the resulting Amplification Curve. After the PCR reaction, the temperature of the reaction solution was gradually increased up to 95° c. from 60° c., and melting curve analysis was performed to obtain a Melt Curve to confirm that that primer dimers were not formed. The sample taken after the real-time PCR measurement was subjected to electrophoresis to confirm that the sequence with 93 bp was amplified out of the gene sequence encoding actin-β from presence of main band around 100 bp.

Results are listed in Table 7. The Cq value was 28.6.

Comparative Example 6

The other conditions and operations were carried out to collect the nucleic acid under the same conditions and by the same operation as in Example 2 except that steps c) and d) were omitted. The amount of collected cell-free DNA was analyzed with respect to the Cq value of the real-time PCR in the same method as in Example 16.

Results are listed in Table 7. From the results, the Cq value was 30.1.

Compared to Example 16, we found that the amount of the cell-free DNA collected from the plasma sample is low while the CQ value is large when steps c) and d) are not performed.

TABLE 7

|  | Washing step 1 | Step c) Anionic surfactant | Washing step 2 | Cq value |
|---|---|---|---|---|
| Example 16 | Tween20 | 0.5% SDS | Tween20 | 28.6 |
| Comparative Example 6 | Tween20 | None | Tween20 | 30.1 |

The invention claimed is:

1. A method of collecting a nucleic acid(s) from a body fluid sample, the method comprising:
    step a) mixing a chaotropic agent and an aluminum oxide support with a water-soluble neutral polymer adsorbed on a surface of the aluminum oxide support with a solution containing a nucleic acid(s), and adsorbing the nucleic acid(s) to the support;
    step b) separating the support on which the nucleic acid(s) is/are adsorbed from the solution mixed at step a);
    step c) mixing the support separated at step b) with a solution containing 0.1 wt % to 2 wt % of an anionic surfactant;
    step d) separating the support on which the nucleic acid(s) is/are adsorbed from the solution mixed at step c); and
    step e) adding an eluent to the support separated at step d) and collecting the nucleic acid(s).

2. The method according to claim 1, wherein the nucleic acid is micro RNA or cell-free DNA.

3. The method according to claim 1, wherein the body fluid sample is blood, serum, plasma, urine, or saliva.

4. The method according to claim 1, wherein the anionic surfactant is of carboxylic acid type, sulfonic acid type, or sulfate ester type.

5. The method according to claim 4, wherein the anionic surfactant of the carboxylic acid type is caprylic acid salt, pelargonic acid salt, capric acid salt, and lauric acid salt, N-decanoylsarcosine salt, or a N-lauroylsarcosine salt.

6. The method according to claim 4, wherein the anionic surfactant of the sulfonic acid type is octylbenzene sulfonate salt or dodecylbenzene sulfonate salt.

7. The method according to claim 4, wherein the anionic surfactant of the sulfate ester type is octyl sulfate salt, decyl sulfate salt, or dodecyl sulfate salt.

8. The method according to claim 1, wherein the water-soluble neutral polymer is a polymer having a zeta potential of not less than −10 mV and not more than +10 mV in a solution of pH 7.

9. The method according to claim 8, wherein the polymer is polyethylene glycol, polyvinyl alcohol, polyvinylpyrrolidone, poly(2-ethyl-2-oxazoline), or hydroxypropyl methylcellulose.

10. The method according to claim 1, wherein the eluent is a buffer solution.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
tgagatgcgt tgttacagga ag                22

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
gtgtggactt gggagagga                19